United States Patent [19]

Pope

[11] Patent Number: 4,805,632
[45] Date of Patent: Feb. 21, 1989

[54] URINE SPECIMEN RECEIVER WITH USER VERIFICATION

[76] Inventor: Herbert J. Pope, 2012 Marshy-Swamp Pt. NW., Knoxville, Tenn. 37932

[21] Appl. No.: 931,252

[22] Filed: Nov. 17, 1986

[51] Int. Cl.$^4$ .............................................. A61B 5/00
[52] U.S. Cl. .................................... 128/760; 128/771; 340/573; 604/318
[58] Field of Search ...................... 128/760, 771, 761; 340/573, 618, 620; 604/318

[56] References Cited

U.S. PATENT DOCUMENTS

| | | | |
|---|---|---|---|
| 2,626,387 | 1/1953 | Berry | 340/573 |
| 3,020,528 | 2/1962 | Swanson, Jr. et al. | 340/573 |
| 4,654,299 | 1/1986 | Ehrenkranz | 128/771 |

*Primary Examiner*—Ruth S. Smith
*Attorney, Agent, or Firm*—Pitts and Brittian

[57] ABSTRACT

A urine specimen container for providing information verifying passage of a donor's urine directly from the urinary tract into the container. The urine specimen container is provided with a plurality (e.g., three) electrical contacts within the container body each spaced at a different distance above the bottom member of the container. A splash shield protects the contacts from the direct impingement of the urine stream. The exterior of the container has a conductive coating applied over at least a portion thereof whereby the hand of a donor will contact this coating. An electrical circuit having two portions is connected between the electrical contacts and the conductive coating. The first circuit portion is connected between the conductive coating and the contact closest to the bottom member of the container, and is responsive to a resistive input corresponding to the resistance from the donor's hand through the body and the urine stream to the contact. This first portion has a first selected time delay. The second portion is connected to the upper two of the three electrical contacts and is responsive to the resistance of urine connecting those two contacts. This second portion has a second selected time delay that is shorter than the first time delay. Interconnection between the circuit portions gives rise to a "true" specimen signal when the first time delay of the first circuit portion expires before any output signal is derived from the second circuit portion. The circuits may utilize integrated chips and are powered by a very low voltage battery.

18 Claims, 2 Drawing Sheets

URINE SPECIMEN RECEIVER WITH USER VERIFICATION

TECHNICAL FIELD

This invention relates generally to containers useful for obtaining samples relative to medical examinations, and more particularly to urine specimen containers having means for identifying actual passage of urine through a person's urinary tract into the container.

BACKGROUND OF THE INVENTION

As an essential portion of most medical examinations, persons are asked to leave a urine specimen for testing. Such examinations may be performed as an incoming or "annual" examination in connection with employment, for example. Furthermore, a "physical" may be required by insurance companies before issuing a policy to a person. One of the principal tests performed on these urine specimens is to detect diabetes, although other illnesses are usually investigated by these tests. More recently, urine specimens are taken for the detection of drugs that are prohibited for certain occupations. Such fields as athletics and security and safety personnel are typical of the fields where drug detection is currently being investigated.

A wide range of containers have been used in the past to receive a urine specimen from a person. Some are glass bottles with a cardboard top that is inserted by the person after passing (voiding) the urine through the urinary tract into the bottle. More recently the container is in the form of a cup having a more secure cover, thus providing additional safety in the shipment of the specimen cup to a laboratory. Because of the hazards of certain illnesses (e.g., AIDS), the cups are often fabricated from plastic and are considered to be disposable. Typical of the cups available for urine specimens are those distributed by American Scientific Products, 1430 Waukegan Road, McGaw Park, Ill. 60085-6787. A typical cup is Model C8827.

One problem that has always been recognized relative to obtaining a urine specimen is that of assuring that the urine deposited in the specimen container is actually that of the person for whom the tests are to be performed. This problem has greatly increased in various drug testing examinations. Due to the requirement for privacy of the person during voiding, there is no assurance that the urine specimen was received from that person at that time or an earlier time—or even from another person. This possible "forgery" of specimens is apparently so prevalent that even a black market in urine specimens has developed.

One attempt at a solution is the use of a urine specimen container that senses the temperature of the urine. Such a device is described in U.S. Pat. No. 4,564,299, issued to J. R. Ehrenkranz on Jan. 14, 1986. Thus, if the temperature of the urine is at a temperature corresponding to the body temperature, there is some assurance that the specimen was voided by the donor directly into the container. However, if a specimen is carried in a container in contact with the body for a period of time, that specimen could achieve a temperature proximate that of body temperature and still not be the specimen of the correct person. With the importance of drug testing, in particular, other precautions are necessary to prevent the introduction of "false" specimens.

Accordingly, it is the principal object of the present invention to provide an apparatus for minimizing the introduction of false urine specimens into the urine collection containers.

It is another object to provide a urine collection container that provides an indication as to whether the urine being deposited in the container is coming through the urinary tract of the container user or whether the urine has another source, e.g., poured into the container.

It is a further object to provide a urine specimen collection container having associated therewith circuitry to provide a signal to differentiate between a specimen that is being received through the urinary tract of a donor or received from another source.

It is also an object of the invention to provide a urine collection container wherein there is an integrally incorporated electrical circuit to provide a signal to differentiate between a urine specimen that is being received through the urinary tract of a user or received from another source.

These and other objects of the present invention will become apparent upon a consideration of the drawings referred to hereinafter and the complete description thereof.

SUMMARY OF THE INVENTION

In accordance with the present invention, there is provided a urine specimen container, preferably in the form of an open cup (with a separate cover), having an electrical circuit incorporated therein which provides a signal which will differentiate between a specimen obtained directly through the urinary tract of a person providing the specimen (a donor) and urine obtained from another source such as being poured into the container. For example, a visible light will be illuminated when the specimen is "true" and no light (or a different light) will be shown when the sample is "false". The circuit includes a path through the body and the urine stream of the donor, and utilizes a power source that is insufficient in current or voltage to be of danger to a donor. A metallic coating on the exterior of the container forms one body contact, and additional contacts are included interior of the cup to complete the electrical circuit.

BEST MODE FOR CARRYING OUT THE INVENTION

Figure 1:
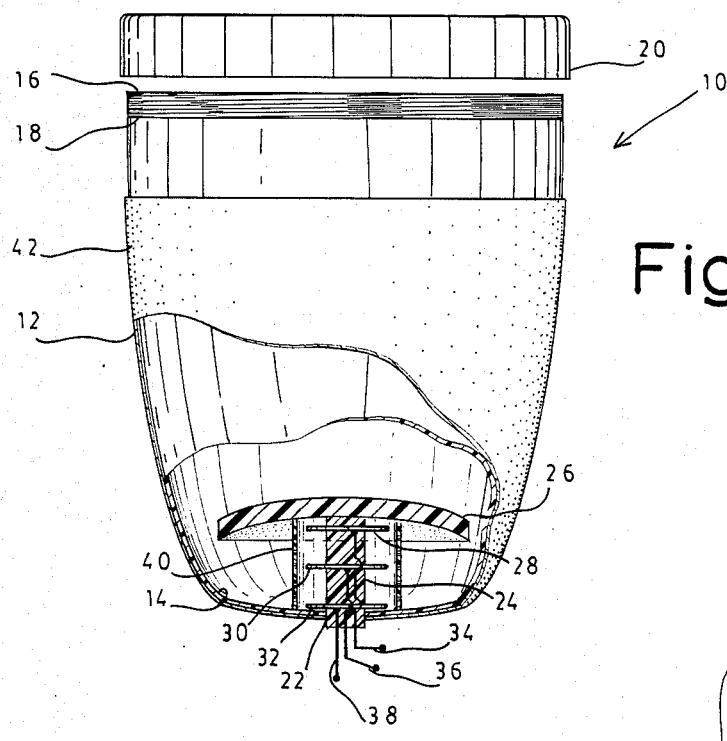
FIG. 1 is a drawing, partially cut away, showing a urine specimen cup generally of conventional design but modified with contacts to accomplish the differentiation of introduction of urine directly from a urinary tract of a donor and urine from another source.

The cup portion of the present invention is shown generally at 10 in FIG. 1. This cup has a generally conical sidewall 12 and a flat or nearly flat bottom 14 as found in typical commercial urine specimen containers. The outer sidewall near the upper rim 16 is typically provided with threads 18 for the engagement of internal threads (not shown) of a screw cap 20. The bottom 14 is provided with a central aperture 22, and mounted through and sealed to this aperture is an upstanding column 24 of an insulating material. This column 24 supports an insulating splash shield 26 and a plurality of electrical contacts proximate the bottom 14 in the form of, for example, spaced-apart disks 28, 30, 32 of conductive material electrically insulated from each other. These disk-like contacts are each spaced a different selected distance above the bottom of the cup body. Leads 34, 36, and 38 connect to these disks, respectively, and become part of the circuit described relative to FIG. 3. If desired, an additional insulating splash shield can be provided in the form of a perforate shield 40 positioned around the periphery of the disks. A further portion of the electrical circuit is provided in the form of a conductive coating 42 applied to at least a portion of the exterior of the sidewall 12. It is to be understood that certain of the components illustrated in FIG. 1 (and FIG. 2) are exagerated in size so as to be more clearly discerned.

Figure 2A:
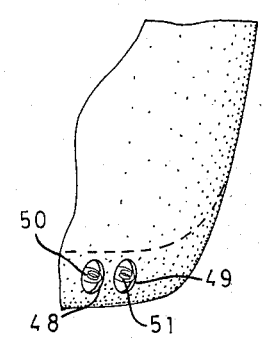
FIG. 2A is a fragmentary drawing showing another embodiment of a base for the urine specimen cup of FIG. 1 illustrating use of a pair of visible output lights.
Figure 2:
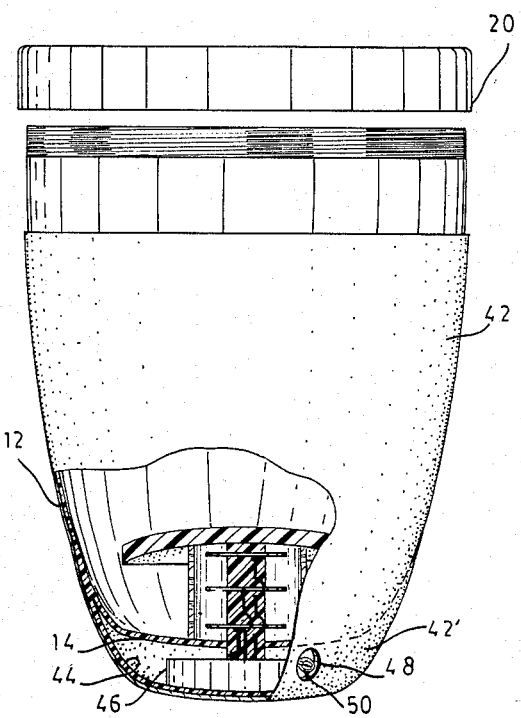
FIG. 2 is a drawing, partially cut away, showing the urine specimen cup of FIG. 1 having a base attached thereto to enclose necessary circuitry for the present invention. This embodiment illustrates use of a single visible output light.

Referring now to FIG. 2, shown therein is a base 44 attached to at least the periphery of the bottom 14. This base 44 contains the necessary circuitry 46 that connect to the leads 34, 36, 38 and to the conductive coating 42. The conductive coating can continue over the exterior of the base 44 as shown at 42'. Typically, the base 44 is provided with at least one opening 48 such that an indicator light (or lights) 50 associated with the circuitry 46 can be viewed.

FIG. 2A illustrates a base having, in addition to the aperture 48, a second aperture 49 with a second light 51 visible therethrough. It will be recognized that for the modification of a commercially available specimen cup, a base containing the electrical circuit may be preferred. However, the electrical circuit can be encased in a protective material and fastened within the cup proximate the bottom. In such a construction, the aperture for the indicator light would be in the wall of the cup.

Figure 3:
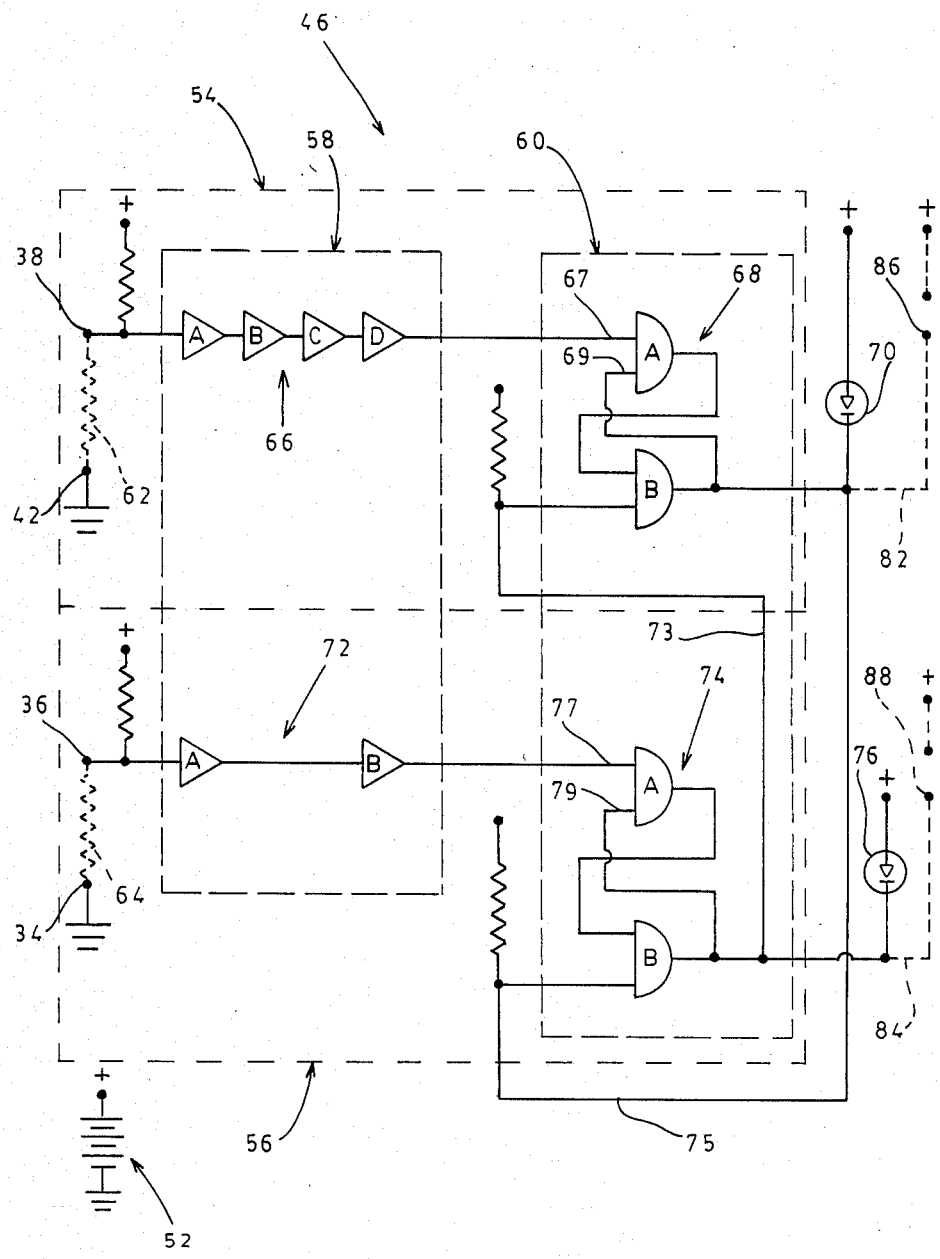
FIG. 3 is a schematic drawing of one embodiment of the circuit used for the present invention.

The schematic diagram of one embodiment of a circuit 46 for achieving the present invention is shown in FIG. 3. The circuit is powered, for example, with a 4.2 volt cell 52. The circuit is divided into components or subcircuits: a section 54 for responding to a "true" urine specimen, and a section 56 for responding to a "false" specimen. The circuit is preferably constructed using two integrated chips identified by the dashed lines 58, 60. It can be seen how the conductive disks 28, 30, 32 and the conductive surface 42 connect into this circuit from this Figure. Indicated at 62 and 64 are the resistor symbols corresponding to the urine specimen while being introduced into the cup 12. Resistor 62 represents the resistance between the hand of a donor in contact with the coating 42, through the donor's body through the urine stream entering the cup and to the contact 32. Resistor 64, which is much smaller, would be that resistance sensed when the urine is introduced from some other source.

Integrated chip 58 is typically a CD40106B Hex Schmitt Trigger available from numerous manufacturers. A first portion 66(A-D) is used to detect the small current (e.g. about 4 microamperes) present when the resistance (resistor 62) of a correct specimen exists between the conductive coating 42 on the exterior of the specimen cup 10 and contact 32 within the cup. After a delay established by the trigger 66 (or other suitable delay networks), a signal is impressed on a first portion 68(A-B) of the second integrated circuit 60 which is typically a 74C00 IC Quad 2-input nand gate chip configured as a "RS" flip-flop circuit. As is known by those skilled in the art, a capacitor 63 assures that nand gate 68A is initially in a "reset" condition. If there is not a second input signal to the second nand gate of this sub-circuit, an output therefrom gates on an indicating light 70 which typically is an LED lamp (typically green). This lamp, which is visible through the base 44 (see FIG. 2), remains illuminated after use of the cup has been completed and the specimen has been given to medical personnel.

If, however, resistor 64 in the "false" specimen circuit 56 is effectively connected between contacts 28 and 30, a signal related thereto is passed by Schmitt trigger 72(A-B) (or other suitable delay network) which is also part of the integrated circuit chip 58 to a second nand gate pain 74. This nand gate fair is also configured as a "RS" flip-flop circuit as will be recognized by those versed in the art. As above, a capacitor 65 is normally used to assure proper initial reset condition of nand gate 74A. If this signal from trigger 72 occurs prior, in time, to the signal from trigger 66, it turns on the second nand gate 74(A-B) of the integrated circuit chip 60 and provides a signal to a second input of the first nand gate 68 via lead 73 preventing an output therefrom and thus preventing illumination of lamp 70. However, if the signal from trigger 66 occurs prior to the signal from trigger 72, the second nand gate 74 is prevented from producing an output therefrom via a signal on lead 75. As is well known, both leads 73 and 75 preferably contain diodes 71, 81, respectively, to always assure proper operation of the flip-flop circuits. When there is an output from the second nand gate 74, a second lamp 76 can be iluminated. This second lamp is illustrated in FIG. 2A and is also typically an LED lamp (typically red). There is less time delay experienced in the Schmitt trigger 72 than in the Schmitt trigger 66 because contacts 28 and 30 become essentially shorted together in use. These contacts, as shown, are higher in the cup. This difference of time delay thus assures that during a "false" specimen, the Schmitt trigger 72 will always trigger first and hold the "true" specimen circuit in the "off" state.

The use of integrated chips in the circuit is, of course, optional; however, their use simplifies construction. It is possible, for example, to produce a single integrated circuit including the components illustrated as being in two chips. Similarly, the use of Schmitt trigger units is optional. Their use provides one means for introducing a selected time delay in the operation of the two nand gates. Other time delay devices are also usable in the present invention. For example, selected resistor-capacitor (R-C) networks are also useful for providing the desired time delays. Specific R-C networks will be apparent to those versed in the art.

The nand gates 68, 74 of the circuit 46 are each used as a "comparator" unit, i.e., they compare the signals at their inputs. For example, nand gate 68A has a pair of input ports 67, 69; input gate 67 is to receive a signal from the first time delay unit 66 and input port 69 is to receive a signal from the output from nand gate 74. If the signal to input port 67 is received before that to input port 69, nand gate 68A will be turned "on" and its output signal will then trigger "on" 68B so as to give—and hold—an output signal from nand gate 68B. Conversely, if a signal is received on the input port 69 before that to input port 67, nand gate 68 wil be kept turned "off".

Nand gate 74 functions in a like manner relative to signals received on its two input ports 77, 79. If there is no signal from nand gate 68, nand gate 74A will be turned on, the signal will "flip" to 74B, there will be an output that is held from nand gate 74B, and nand gate 68 will be kept "off".

It will be recognized by those versed in the art that other known comparator units can be used in place of the nand gates illustrated in the present invention. Therefore, the present invention is not limited to such nand gates; however, they are easily adapted for the invention. Whatever comparator unit is used should have a "hold" feature such that whatever output signal is generated will be held sufficiently to indicate a "true" or a "false" urine specimen.

Figure 2B:
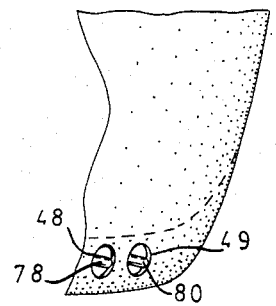
FIG. 2B is a fragmentary drawing showing another embodiment of a base for the urine specimen cup of FIG. 1 for use with a separate device to provide an indication of validity of the specimen.

Although lamps are illustrated to indicate a "true" or "false" specimen, the present invention is not to be limited to this type of "output". For example, as illustrated in FIG. 2B there can be contacts 78, 80 built into the base 44 at the apertures 48, 49 whereupon these contacts can be mated with an external indicator circuit. Connections to such contacts are illustrated in FIG. 3 with the lines 82, 84. It will be recognized that other forms of "output" signal can be used to indicate a "true" or "false" specimen. One such "readable" output would be infra-red LED lamps instead of visible lamps.

In a normal use of the present invention, the specimen cup will be given to a person (the donor) from whom the specimen is desired. The lamp (or lamps when two lamps are used) will not be illuminated at this time. The donor then, in the privacy of a rest room, voids into the cup and returns the same (after covering) to the medical personnel. If no lamp is illuminated, or if the false specimen lamp is illuminated, the donor is then asked to leave another specimen. No explanation needs to be given under these circumstances. If the green light is illuminated (or a corresponding signal is obtained), the specimen is identified as a "true" specimen, and the specimen can be sent for analysis.

From the foregoing, it will be recognized by persons versed in the art that a urine specimen container has been provided by the present invention that substantially reduces the possibility of obtaining a specimen that is not that of the person for whom any analysis is desired. The circuitry thereof is sufficiently low in cost that, even for disposable containers, this cup can be manufactured for mass use in urine analysis for whatever purpose. Although only one basic construction is described, with certain minor modifications, the present invention is not to be limited to this embodiment. Rather, the invention is to be limited only by this description taken together with the appended claims and their equivalents.

I claim:

1. A container for the collection of a urine specimen of a donor, which comprises:
   a collector body to receive a urine stream from said donor, said collector body having a side wall with a top rim defining an opening into said collector body, and a bottom member joined to said side wall;
   a conductive coating applied to at least a portion of the exterior of said side wall of contact with a hand of said donor;
   three spaced-apart electrical contacts mounted upon an insulative support within said container proximate said bottom member, each of said contacts being a different selected distance from said bottom member; and
   a shield mounted upon said support positioned proximate said electrical contacts in a direction toward said rim, said shield preventing direct deposit of said urine stream upon said eletrical contacts.

2. The container of claim 1 further comprising:
   an electrical circuit positioned proximate and external said bottom member, said electrical circuit including electrical leads from said electrical contacts which penetrate said bottom member and are sealed thereto, said circuit further including means adapted to be responsive to both a first selected resistive input corresponding to a resistance from said hand of said donor through said donor's body and said urine stream to one of said electrical contacts within said container, and to a second selected resistive input corresponding to a resistance when urine is not directly passing through said urinary tract, said electrical circuit providing at least one signal corresponding to an output when said first selected resistive input is sensed by said circuit; and
   a base member enclosing said electrical circuit, said base member joined to said bottom member.

3. The container of claim 2 wherein said insulative support is an insulating column upstanding within said body from said bottom member, and said electrical leads pass through said insulating column to said electrical circuit.

4. The container of claim 2 wherein said three electrical contacts are a first contact most adjacent said bottom member, a second contact most removed from said bottom member, and a third contact positioned intermediate said first and second contacts, and wherein said electrical circuit comprises:
   a first input connected to said first contact;
   a second input connected to said conductive coating, said second input being at chassis ground in said electrical circuit;
   a third input connected to said third contact;
   a fourth input connected to said second contact, said fourth input being at chassis ground in said electrical circuit;
   a first time delay circuit having a first selected time delay connected to said first input;
   a first comparator connected to an output of said first time delay circuit, said first comparator adapted to provide a signal to an output when an input is received only from said first time delay circuit;
   a second time delay circuit having a second selected time delay less than said first selected time delay connected to said second input;
   a second comparator connected to an output of said second time delay circuit, said second comparator having an output connected to second input to said first comparator and adapted to provide an output signal when an input is received from said second time delay circuit prior to an input from said first time delay circuit; and an output element connected to said output of said first comparator, said output element actuated when said output signal is received from said output of said first comparator.

5. The container of claim 4 wherein said first time delay circuit is four Schmitt trigger members in series, said second time delay circuit is a pair of Schmitt trigger members in series, said first comparator is a first nand gate pair configured as an RS flip-flop circuit, and said second comparator is a second nand gate pair configured as an RS flip-flop circuit.

6. The container of claim 4 wherein said output element is an indicating lamp mounted within said base and visible from exterior said base to be illuminated upon receipt of an output signal from said first comparator.

7. The container of claim 4 further comprising a second output element connected to said output of said second comparator.

8. The container of claim 7 wherein said second output element is an indicating lamp mounted within and visible from exterior said base to be illuminated upon receipt of said output signal of aid second comparator.

9. The container of claim 4 further comprising an interconnection between said output of said first comparator and a second input to said second comparator for preventing said output signal from said second cmoparator when said first comparator produces an output signal.

10. The container of claim 1 further comprising a removable cover for said opening of said collector body.

11. A container for the collection of a urine specimen of a donor, said container providing means for identifying actual passage of a urine stream from said donor's urinary tract directly into said container, which comprises:

a collector body to receive said urine stream from said donor, said collector body having a side wall with a top rim defining an opening into said collector body, and a bottom member;

a conductive coating applied to at least a portion of the exterior of said side wall for contact with a hand of said donor;

an insulating column within said body upstanding from said bottom member;

three electrical contacts supported from said insulating column with a first electrical contact being most adjacent said bottom member, a second electrical contact most removed from said bottom member and a third contact positioned intermediate said first and second contacts;

a splash shield mounted on a top extremity of said insulating column, said splash shield preventing direct deposit of said urine stream upon said electrical contacts;

a first electrical circuit connected between said conductive coating and said first electrical contact, said first electrical circuit including means adapted to be responsive to a first resistive input corresponding to a resistance from said hand of said donor through the donor's body and said urine stream to said first electrical contact, said first electrical circuit including a first time delay means having a first selected time delay in transmitting a signal produced by said first resistive input and a first comparator connected to said first time delay means;

a second electrical circuit connected between said second and third electrical contacts, said second electrical circuit including means adapted to be responsive to a second resistive input corresponding to a resistance from said second electrical contact through urine in said collector body to said third electrical contact circuit, said second electrical circuit including a second time delay means having a second and shortened selected time delay in transmitting a signal produced by said second resistive input, and a second comparator connected to said second time delay means;

circuit means connecting said second electrical circuit to said first electrical circuit whereby an output signal of said second electrical circuit disables said first electrical circuit when said output signal of said second electrical circuit occurs prior to expiration of said first time delay of said first electrical circuit, and an output of said first comparator disables said second electrical circuit when expiration of said first time delay of said first electrical circuit occurs prior to expiration of said second time delay of said second electrical circuit; and a first output member connected to an output of said first electrical circuit, said output member providing a signal indicating a specimen directly from said donor's urinary tract when expiration of said first time delay of said first electrical circuit expires prior to expiration of said second time delay of said second electrical circuit.

12. The container of claim 11 further comprising a second output member connected to an output of said second electrical circuit to provide an output signal indicating a false specimen when expiration of said second time delay of said second electrical circuit occurs prior to expiration of said first time delay of said first electrical circuit.

13. The container of claim 12 wherein said first and second electrical circuits are contained in a base member attached exterior to said bottom member, and said first and second output members are lamps of differing color visible from exterior said base member.

14. The container of claim 11 wherein said first and said second electrical circuits are contained in a base member attached exterior to said bottom member, and said first output member is a lamp visible from exterior said base member.

15. The container of claim 11 further comprising a removable cover for said opening of said body.

16. The container of claim 11 wherein:

said time delay means of said first electrical circuit is four Schmitt trigger units in series, and said first comparator of said first electrical circuit further is a first nand gate pair configured as an RS flip-flop circuit whereby an output is obtained from said first electrical circuit when only an input of said first nand gate pair connected to said time delay means is energized; and said time delay means of said second electrical circuit is two Schmitt trigger units in series, and said second comparator of said second electrical circuit is a second nand gate pair configured as an RS flip-flop circuit whereby an output is obtained from said second circuit when only an input of said second nand gate pair connected to said second time delay means is energized.

17. The container of claim 16 wherein said first and said second Schmitt trigger time delay units are within a single first integrated circuit chip, and said first and said second nand gate pairs are within a single second integrated circuit chip.

18. The container of claim 16 wherein said first and second Schmitt trigger time delay units and said first and second nand gate pairs are within a single integrated circuit chip.

* * * * *